United States Patent
Moe et al.

[11] Patent Number: 5,457,319
[45] Date of Patent: Oct. 10, 1995

[54] PROCESS FOR MEASUREMENT OF THE DEGREE OF CURE AND PERCENT RESIN OF GLASS-FIBER REINFORCED EPOXY RESIN PREPREG

[75] Inventors: Amy L. Moe, Holmen; Jiri D. Konicek, Onalaska, both of Wis.

[73] Assignee: AlliedSignal Inc., Morris Township, Morris County, N.J.

[21] Appl. No.: 239,072

[22] Filed: May 6, 1994

Related U.S. Application Data

[63] Continuation-in-part of Ser. No. 71,128, Jun. 2, 1993.
[51] Int. Cl.[6] .................................................. G01N 21/35
[52] U.S. Cl. .................................. 250/339.12; 250/341.1
[58] Field of Search ........................... 250/339.12, 341.1

[56] References Cited

U.S. PATENT DOCUMENTS

| | | | |
|---|---|---|---|
| 3,970,393 | 7/1976 | Krygeris et al. | 356/195 |
| 4,582,520 | 4/1986 | Sturm | 250/339.12 |
| 4,609,628 | 9/1986 | Aschenbeck | 250/339.12 |
| 4,769,544 | 9/1988 | Dahlquist | 250/339.12 |
| 5,142,151 | 8/1992 | Varnell et al. | 250/339.12 |

FOREIGN PATENT DOCUMENTS

| | | |
|---|---|---|
| 0164291 | 11/1985 | European Pat. Off. . |
| 0453797A3 | 10/1991 | European Pat. Off. . |
| 2044443 | 10/1980 | United Kingdom . |
| WO91/07650 | 5/1991 | WIPO . |
| WO92/18847 | 10/1992 | WIPO . |
| WO84/01430 | 4/1994 | WIPO . |

*Primary Examiner*—Carolyn E. Fields
*Attorney, Agent, or Firm*—Harold N. Wells; Roger H. Criss

[57] ABSTRACT

The degree of cure and the amount of epoxy resin in a glass fiber reinforced epoxy resin prepreg is measured by exposing the prepreg to a series of light pulses created by optical filters transmitting light at predetermined bandwidths about selected wavelengths, preferably centered at wavenumbers of about 4529 $cm^{-1}$ and 4055 $cm^{-1}$ and measuring the amount of epoxy groups and methyl groups present relative to reference values from the electrical pulses produced by a phase sensitive photoelectric detector disposed to receive said light pulses after being exposed to said prepreg. When such measurements are made in a continuously moving sheet of prepreg, it is possible to control the variation of percent cure and resin content to no greater than ±3% cure and ±3% resin content over a distance of at least 400 yds (366 m).

9 Claims, 1 Drawing Sheet

PROCESS FOR MEASUREMENT OF THE DEGREE OF CURE AND PERCENT RESIN OF GLASS-FIBER REINFORCED EPOXY RESIN PREPREG

CROSS-REFERENCE TO RELATED APPLICATIONS

This is a continuation-in-part of U.S. application Ser. No. 08/071,128, filed Jun. 2, 1993.

BACKGROUND OF THE INVENTION

The invention relates generally to the manufacture of prepregs, that is, partially cured sheets of fabric-reinforced thermoset resins. Most commonly, these are woven fabrics of glass fiber which are coated with epoxy resins and then partially cured. Such prepregs are used to fabricate laminates for the production of the printed circuit boards found in countless consumer products.

The quality of the prepregs is determined among other things by the uniformity of the product. One important measurement is the degree to which the resins have been cured, since they are intentionally only partly cured. The prepregs are usually produced on large pieces of equipment ("treaters") which continually apply resins to fiberglass fabric and then partially cure it by heating. The rolls of fabric may be about 3.2 to 4.2 feet (1–1.3 m) wide and up to about 3000 to 7800 feet (914–2377 m) long. It will be obvious that significant variations in the amount of resin applied to the fabric could occur over the time that such large rolls of fabric are handled. If the amount of the resin varies, then variations in the degree of cure may result even if otherwise the conditions are uniform. In addition, the degree to which the resins are cured may vary depending on the amount of heat received by the wide "web" of fiberglass as it passes through the treater.

Another source of variation in the quality of the prepregs is the composition of the resins themselves for they typically comprise mixtures of epoxy compounds along with curing agents. If the quality of the raw materials varies, then the degree of cure achieved may vary as well. Those familiar with the art will understand that such variations in quality do occur, making uniformity difficult to obtain.

Still another source of non-uniformity of prepregs is the variations in the fabric. If the fabrics are not uniform the amount of resin applied will be affected and the degree of cure of the resin in the finished prepreg as well.

While infrared spectroscopy has been applied to measuring the degree of cure of polymers such as epoxy resins, continuous on-line application to large size commercial prepregging equipment is a difficult task and not heretofore practiced successfully so far as is known. The reasons for this are many, including all the inherent variations in the process described above and the difficulties associated with on-line application of an analytical instrument.

The degree to which prepregs are cured is the subject of U.S. Pat. No. 5,142,151, which discusses a method of determining the degree of resin cure and its application to commercial equipment for coating fabrics with thermoset resins and then partially curing them. The method used involves the measurement of the degree of resin cure by infrared spectroscopy, particularly using the type of equipment called FTIR (Fourier Transform InfraRed).

The process generally described in U.S. Pat. No. 5,142,151 involves passing a beam of infrared light through or against a moving glass fiber web which is coated with a partially cured resin and then determining the degree of cure by the absorption centered at certain wavelengths of infrared light. Wavelengths were identified which were associated with the reactive epoxy groups and with methyl groups (which do not react) and could be used to determine the amount of resin present and the degree of epoxy cure. The epoxy and methyl groups were shown to absorb in the regions centered at about 4529 and 4060 wavenumbers ($cm^{-1}$). The FTIR instrument measures the amount of light absorbed in the regions centered about the selected wavelengths and then mathematically manipulates the data to calculate the degree to which the resins have been cured and the amount of resin present. It is shown in the '151 patent that the absorbance at the chosen frequency can be related to the gel time (a standard test for the degree of cure of epoxy resins, IPC Test Method 2.3.18) or the flow testing method (another standard test, IPC Test Method 2.3.17). Such traditional methods available in the art for measuring the curing characteristics of resin formulations are imprecise and require a consistency of technique which is difficult to achieve.

The disadvantage of using FTIR is that it is relatively slow so that continuous traverse of a moving prepreg sheet is impractical. As shown in U.S. Pat. No. 5,142,151 with multiple light sources and receivers it could be implemented, although costly. However, only specific locations across the web could be sampled.

Once the degree of cure has been determined it is then feasible to make adjustments in the prepreg equipment to advance or retard the cure and to correct for variations in the equipment performance to the extent that the equipment permits. A number of such adjustments are illustrated in the '151 patent, including changing the temperature to which the coated glass fiber web is exposed, adjusting the speed of the web, correcting the amount and uniformity of the resin on the fabric, and changing heat input from the local heating elements.

The present invention represents improvements to the general process disclosed in the '151 patent which make possible production of prepregs of a uniformity not previously available. In particular, the invention relates to the use of continuous on-line monitoring of a moving web of prepreg using infrared spectroscopy.

SUMMARY OF THE INVENTION

The invention includes a process for continuously measuring the degree of cure and resin content of a moving sheet of glass fiber-reinforced epoxy resin prepreg and controlling such measured variables.

The process employs the dispersive method of infrared spectroscopy wherein a beam of infrared light is sequentially intercepted by a series of optical filters which transmit light only in a predetermined bandwidth about wavelengths corresponding to absorption by epoxy groups and methyl groups, particularly absorption centered at wavenumbers of 4529 $cm^{-1}$ for epoxy groups and 4055 $cm^{-1}$ for methyl groups. To account for any changes which may occur not related to the curing of epoxy groups reference values are measured for comparison, particularly at about 4587 $cm^{-1}$ and 4496 $cm^{-1}$ for epoxy groups and 4119 $cm^{-1}$ and 4011 $cm^{-1}$ for methyl groups. The bandwidth for each of these wavenumbers is chosen to most accurately provide values for the variables being measured. The bandwidth is less than a total of 1%, preferably about 0.7–0.9% of the center values, e.g., 4529 cm$^{-1}$ for epoxy groups. The light pulses which are generated are passed through the moving prepreg sheet and then received by a photoelectric detector which produces a series of electrical pulses at voltages proportional to the intensity of the light received. After correction for the inherent absorbance of the glass fiber and epoxy resin being used, these electrical pulses are used to compute amounts of epoxy and methyl groups and then the degree of cure and the amount of epoxy resins. Preferably, the degree of epoxy cure is computed from the ratio of epoxy groups to methyl groups relative to the ratio in an unreacted epoxy resin formulation. The resin content is computed from the amount of methyl groups relative to the amount expected to be in the prepreg based on the resin used.

The process described is continuously repeated as the beam of infrared light is continually moved so as to traverse the width of the moving prepreg sheet. The calculated results are displayed, preferably on a video terminal, and compared with predetermined standard values. Adjustments are made to provide the desired degree of cure by changing the residence time and temperature used to partially cure the prepreg and to provide the desired resin content by changing the amount of uncured resin applied to the glass fiber sheet.

The invention makes it possible to produce a partially-cured glass fiber-reinforced epoxy resin prepreg having a variation of percent cure and resin content no greater than 4–3% cure and 4–3% resin content over a distance of at least 400 yds (366 m).

In preferred embodiments the measured degree of cure and resin content is compared with a standard prepreg mounted at the edges of the prepreg sheet where measurements are being made. Automatic control of treater temperature and residence time is preferred, based on the measurements. In one aspect this includes adjustment of the treater conditions based on measurements made of uncured coated fabric which is to be convened into prepreg.

DESCRIPTION OF THE PREFERRED EMBODIMENTS

Infrared Analysis

Figure 1:
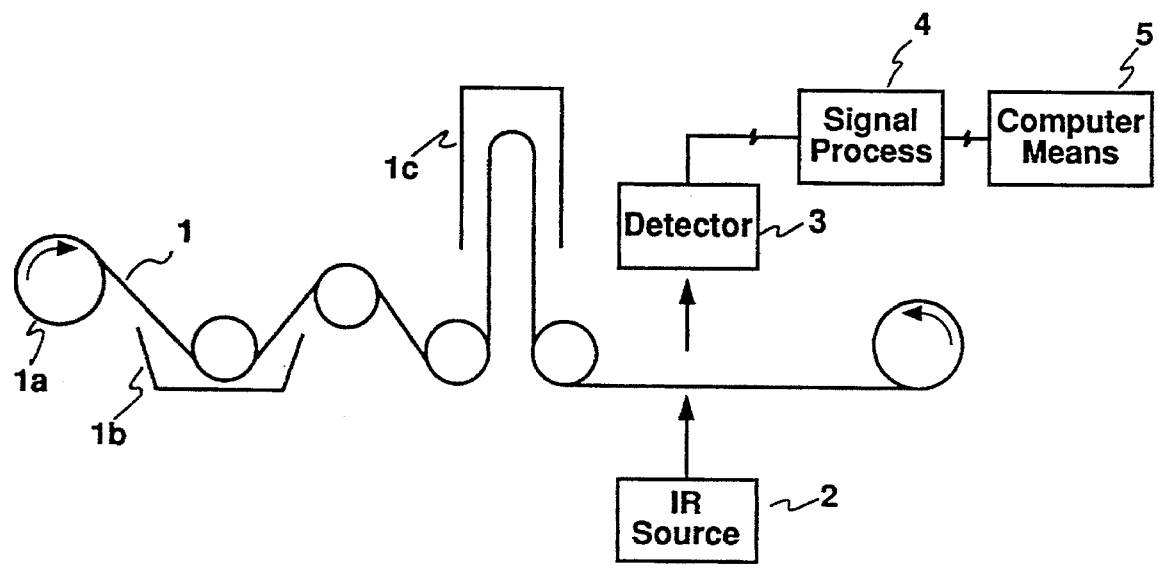
FIG. 1 is a schematic view of an apparatus for producing glass fiber-reinforced epoxy resin prepreg.

As explained in U.S. Pat. No. 5,142,151 the degree of cure of resins is established by exposing the resin and the reinforcing fabric to light in the infrared region and then measuring the amount of such light which is absorbed by the resin and the fabric. The resin and fabric each have characteristic frequencies at which they absorb the infrared light. For epoxy resins the wavelength centered about the peak at 4529 cm$^{-1}$ wavenumber is recommended in the '151 patent. Glass fiber absorbs infrared light at about 2000 cm$^{-1}$ and therefore does not interfere with the measurement of the epoxy and methyl groups, although the glass fiber will affect the total light transmitted and thus the apparent absorption at the wavenumbers corresponding to epoxy and methyl groups. The fiber glass also scatters the light and introduces "noise" in the measurements. For this reason, adjustments for the inherent absorbance of the glass fiber and epoxy system being cured are made. A baseline value representative of the amount of resin is needed for comparison with the epoxy measurement to assure that any change in the epoxy value is due to curing (i.e. reaction of the epoxy groups) rather than to a change in the amount of resin present. The methyl groups have been recommended as the reference. Methyl groups absorb light at a wavelength centered at about 4060 cm$^{-1}$ wavenumber.

The absorption of infrared light at the desired frequencies is monitored by a phase sensitive photodetector of the types known in the art, such as photomultiplier tubes, photodiodes, photoconductive and photovoltaic semiconductors, and thermal detectors. The electrical output of the detector is used to compute the ratio of epoxy groups to methyl groups, which are then used to calculate the degree of cure and the amount of resin present on the web.

The preference in the '151 patent is for use of the FTIR instrument which provides a reading across the entire spectrum of the infrared source. The absorption peaks characteristic of the degree of cure (i.e., epoxy) and the amount of resin (i.e., methyl) are used to make the necessary calculations. In the present invention, the dispersive method is employed, which involves the use of filters which permit only light having a predetermined bandwidth about the selected wavelengths to pass to the detector, thus in effect limiting the detector output to the peaks of interest. While this method has some disadvantages, namely "drift" as described in the '151 patent, it is less costly and is easier to apply to on-line inspection. Although infrared measurements can be made off-line, that is, on samples of prepreg taken from the web being produced, it is highly desirable to directly measure the prepreg as it is being produced. If this can be done rapidly enough as it is in the dispersive method, it becomes possible to measure all of the web and to apply continuous and automatic control of the equipment as generally disclosed in the '151 patent.

Use of the dispersive method of measuring the degree of cure requires the manufacture of filters which pass light only within a band centered at the desired wavenumber, which provides a reading equivalent to the area under the curves as shown in the '151 patent. The optimum bandwidth is that which most closely represents the values determined by other conventional techniques. The recommended bandwidth is less than a total of 1% of the center value, preferably about 0.7–0.9%. Once the desired properties of the filters are defined the filters can be manufactured by techniques known to those skilled in the art. The filters are passed in a fixed sequence between the source of the infrared light and the web or between the web and the photodetector. This makes it possible to obtain a series of responses from the photodetector which represent the epoxy and methyl groups present in the portion of the web being examined. More than one filter of each type may be provided to improve precision of the readings. In addition, reference filters which read the degree of absorption at the base of the absorption peak for the epoxy and methyl groups will be used to provide corrections as conditions change.

It has been found that in applying the dispersive technique to continuously moving sheets of epoxy prepreg that rather than using a single predetermined reference wavenumber as a baseline value as suggested in the parent of this application, that reference measurements at the base or "shoulders" of the epoxy and methyl peaks should be made and used instead. The preferred values are about 4587 cm$^{-1}$ and 4496 cm$^{-1}$ for the epoxy peak and 4119 cm$^{-1}$ and 4011 cm$^{-1}$ for the methyl peak, but these could be modified as necessary to provide the most accurate results. The bandwidths of the reference wavenumbers should be about the same as those preferred for the epoxy and methyl groups as discussed above.

The light passes through the resin coated glass fiber web as a series of pulses which correspond to the light absorbed by the epoxy groups and methyl groups present in the partially cured resin. The amount of light absorbed in the regions centered about 4529 cm$^{-1}$ and 4055 cm$^{-1}$ provides a measure of the amount of epoxy and methyl groups in the resin. It should be understood that passage of the light through the web will cause attenuation and scattering of the light generally, which will affect the output of the photoelectric detectors. These effects will be ignored in this description but they are accounted for in the processing of the data produced by the detector. As the epoxy resin is cured in the treater the light passing through the web centered at 4055 cm$^{-1}$ should not change since the methyl groups are non-reactive. However, the number of epoxy groups diminishes and accordingly, the amount of light centered at 4529 cm$^{-1}$ increases in proportion to the fraction of the epoxy groups which have been reacted. Thus, the series of electrical voltages produced by the detector corresponding to the light received at 4529 cm$^{-1}$ can be compared with those received at 4055 cm$^{-1}$ and the % cure (i.e. the % epoxy groups which have disappeared) calculated. The reference filters which pass light at a wavelength adjacent the epoxy and methyl group values provide a baseline reference against which the degree of cure and resin content are determined.

Although other computations are possible, it is preferred that the ratio of epoxy groups to methyl groups is determined. The amounts are proportional to the logarithm of the voltage corresponding to the light pulse centered at 4529 cm$^{-1}$ (epoxy) divided into the logarithm of the voltage corresponding to the light pulse centered at 4055 cm$^{-1}$ (methyl) and corrected by the logarithm of the voltage corresponding to the light pulses centered at values on at least one shoulder of the epoxy and methyl peaks. This relationship may be expressed as:

$$\frac{E}{M} = \frac{\text{epoxy}}{\text{methyl}} = \frac{(K_1 \log I_{4055})}{(K_2 \log I_{4529})}$$

where:
E/M is the ratio of epoxy to methyl groups
$K_1$ and $K_2$ are correction factors
I is the voltage output corresponding to the light received centered at the subscript wavenumber
A correction of this ratio will be made if the voltage output corresponding at the reference wavenumber changes. The degree of epoxy cure is calculated from the expression $$\frac{\left(\frac{E}{M}\right)_i - \left(\frac{E}{M}\right)_f}{\left(\frac{E}{M}\right)_i} \times 100$$

where:
i represents the initial ratio in uncured resin
f represents the final ratio in partially cured resin
The amount of resin in the prepreg may be determined as proportional to the logarithm of the voltage corresponding to the light pulse at 4055 cm$^{-1}$ (methyl). This may be expressed as:

$$\% \text{ resin} = K_3 \frac{1}{\log I_{4055}}$$

where:
$K_3$ is a correction factor
I is the voltage output corresponding to the light received centered at the subscript wavenumber
Again, a correction may be necessary if the voltage output corresponding to the reference wavenumber (s) changes.

Control of the Prepreg Equipment

The '151 patent provides a general description of the typical equipment used in the preparation of prepregs. It may be briefly summarized as follows. A roll supplies the treater with fabric which is first coated with resin, usually by dipping the fabric into a bath of the resin and then passing the coated fabric through rollers which remove the excess resin and make the coated fabric as uniform as possible. The coated fabric then is passed through a region in which it is heated by hot air and/or radiant heaters. During the passage through the heated region solvent is evaporated, the temperature of the coated fabric is increased, and the resin cure proceeds. Typically, the temperatures rise to about 150° C. The residence time and the temperature are important variables which determine the degree of cure which is obtained. After curing the web is cooled and rewound or cut into pieces for storage before later being used to make fully cured laminates.

Control of the degree of cure can be obtained by methods generally described in the '151 patent. Preferably, the treater conditions can be adjusted to provide temperatures as required to portions of the web so that uniform curing is obtained. The ability to accomplish close control of the cure across the web will depend on the equipment available.

If the method is to be used successfully, the behavior of the resin formulation must also be known. It is necessary to formulate the resin composition so that its initial infrared signature is established and thus to provide a reference point for the change in infrared absorption as the resin is cured. In practice this is done by experimenting with the resin and its curing agents off-line so that accurate information is available to establish the basis for control of the curing process in the continuous equipment. Ideally, each batch of resin formulated should be sampled and its composition adjusted to correspond to the standard used to measure degree of cure. Alternatively, the standard could be adjusted so that the degree of cure is correctly related to the measurements.

EXAMPLE

A particularly favored embodiment incorporates some aspects of infrared gauges familiar to those skilled in the art but also includes features which have been found important to successfully applying infrared gauging to the preparation of epoxy prepregs.

FIG. 1 illustrates conceptually the equipment of the invention. The moving web (1) of glass fabric coated with an epoxy resin formulation is shown moving from left to right in the equipment, which is commonly called a "treater" in the industry. A roll of glass fiber fabric (1a) is unrolled, dipped into a bath of an epoxy resin formulation (1b) and then passed into a heated region (1c) where the solvents are evaporated and the epoxy resins are partially cured. While the infrared gauging equipment (2–5) might be placed within the treating equipment, it is preferred to locate it at the output end so that finished prepreg is measured for its degree of cure. The environment within the treater is relatively harsh and could interfere with operation of the infrared gauge or at least make maintenance more difficult. Although only the product prepreg may be measured, in one embodiment the properties of the freshly coated fabric are measured before heating for comparison with the partially cured product to provide a basis for adjusting the treater conditions. Alternatively, the properties of the coated fabric can be measured and used to adjust the treater conditions needed to achieve the desired product quality. The infrared source (2) emits a pulsed beam of infrared light of a frequency determined by the characteristics of the filters, as will be discussed in more detail below. The light passes through the moving web (1) and is partially absorbed and scattered by the resin and the glass fibers of the fabric. The emerging light enters a light sensitive detector (3) where it is converted into a voltage proportional to the light intensity. The output of the detector is sent to the signal processor (4) where the signals which correspond to the measurements of epoxy cure and resin content are derived, corrected for the type of glass fiber and epoxy resin being processed, and then sent to the computing means (5) for conversion to values which are used either manually or automatically to adjust the operation of the treating equipment as has been discussed. The infrared light source (2) preferably will be located directly above or below the phase sensitive detector (3) and the pair will transverse the width of the moving web.

Figure 2:
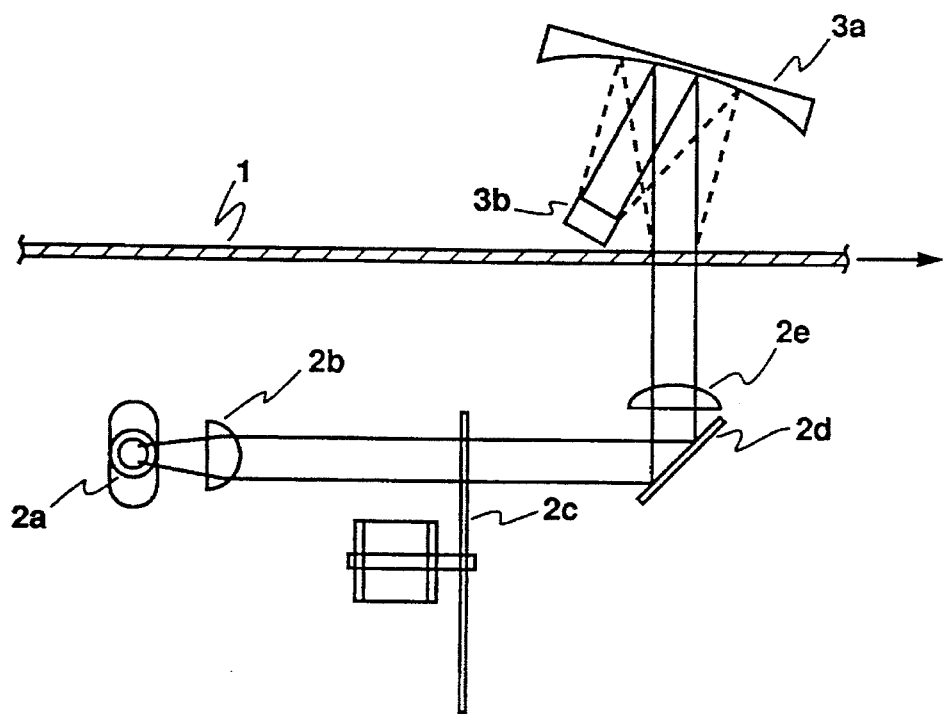
FIG. 2 is a schematic diagram of the infrared measuring instrument of the invention.

FIG. 2 illustrates the infrared light source (2). In this general description the light source follows conventional practice in using a halogen or other suitable source of infrared light (2a), which is directed by a lens (2b) as a beam which impinges on a rotating disc (2c) which contains at least four but typically five or six narrow band filters selected to correspond to the wavelengths of the epoxy and methyl groups in the resin plus at least one reference wavelength for each selected as a baseline against which the epoxy and methyl groups can be measured. In the preferred embodiment at least one of the wavenumbers 4119 cm$^{-1}$ and 4011 cm$^{-1}$ are used as reference for the methyl group value, 4055 cm$^{-1}$, and used to determine the amount of methyl groups present in the resin which correlates with the amount of resin on the web. At least one of the wavenumbers 4587 cm$^{-1}$ and 4496 cm$^{-1}$ are used as reference for the epoxy group value, 4529 cm$^{-1}$, and used to determine the amount of epoxy groups which correlates with the degree of cure of the resin.

While it is possible to use only single filters for each of the wavenumbers as just described it is preferred to use more than one filter for the epoxy and methyl groups in order to minimize the variation in measurements. Since the moving web advances during the time the two filters for each wavenumber being measured rotate into position it can be seen that some additional averaging of the measurements is also obtained. The region of the web which is examined is about 0.5 inches (12.7 mm) wide and elongated by the movement of the web to about 25 mm. The exposure of the web to a single rotation of the disc which contains the filters typically takes about 1.0 second but this could be varied as desired within the capability of the detector to produce a voltage from each of the filters in turn.

It will be evident from this discussion that in a preferred embodiment two filters will be provided for each of the epoxy and methyl group wavenumbers and two reference filters for each, making a total of eight filters. However, in practical applications, it may be necessary to use less than the preferred number of filters, for example, one filter each for the epoxy and methyl group wavenumbers and one or two reference filters for each.

Although a single phase sensitive detector could be used, it is preferred to use a second detector at the light source (not shown) also in order to provide a baseline measurement of the ambient conditions for comparison with the output of the detector receiving the light which has passed through the web. The difference between the output of the receiving detector and the baseline detector is thus the value attributed to the absorption of the web including the glass fibers and the resin. Since the glass fibers absorb at wavenumbers lower than the resin, the glass does not interfere directly with the resin measurements. However, the intensity of the light received by the detector is affected due to absorption and scattering and this must be accounted for in determining the amount of resin on the web and the amount of epoxy cure. Accordingly, it is necessary to compensate for the type of glass fiber and the absorption of the resin. In practice, this means that for each type of glass fabric a correction must be made based on previously determined characteristics of the materials being used. This may be done by off-line measurements using samples of the fabric and the resin formulation. In a preferred embodiment, the paired light source and detector pass off the edge of the web and read the properties of a standard strip of prepreg located to provide a continual reference against which the web can be measured.

We claim:

1. A process for continuously measuring and controlling the degree of cure and resin content of a moving sheet of partially cured glass fiber reinforced epoxy resin prepreg comprising:

(a) passing a beam of infrared light thorough a sequence of optical filters transmitting light only at wavenumbers 4529 cm$^{-1}$ and 4055 cm$^{-1}$ representative of epoxy and methyl groups respectively and at least one reference wavenumber for each of the epoxy and methyl group wavenumbers, each filter having a predetermined bandwidth of less than 1% about said wavenumbers to create a series of light pulses;

b) directing said series of light pulses through a moving sheet of said glass fiber reinforced epoxy resin prepreg;

c) receiving said series of light pulses emerging from said prepreg sheet by contact with a photoelectric detector responsive to said light pulses and producing a series of electrical pulses having voltages proportional to the intensity of the light pulses received;

d) adjusting the voltages of (c) to correct for the inherent absorbance of said glass fiber and epoxy resin;

e) computing the amounts of epoxy groups and methyl groups as proportional to the logarithms of the corrected voltages of (d) and further corrected by the logarithm of the voltage of said reference wavenumbers;

f) computing the degree of cure from the amounts of epoxy groups and methyl groups of (e);

g) computing the amount of epoxy resin in said prepreg as proportional to the corrected voltage of (d) corresponding to the methyl groups as further corrected by the logarithm of the voltage of said reference wavenumber;

h) repeating steps (a)–(g) while continually traversing the width of said prepreg sheet with said beam of infrared light;

i) displaying the results of steps (a)–(h);

j) comparing the measured degree of cure and percent resin displayed in (i) with predetermined standard values; and k) adjusting the degree of cure by the residence time and temperature used to partially cure said prepreg and adjusting the percent resin by the amount of uncured resin applied to said sheet.

2. The process of claim 1 wherein two of said reference wavenumbers are used for each of said epoxy and methyl group wavenumbers.

3. The process of claim 2 wherein said reference wavenumbers for said epoxy group wavenumber are about 4587 cm$^{-1}$ and 4496 cm$^{-1}$.

4. The process of claim 2 wherein said reference wavenumbers for said methyl group wavenumber are centered at about 4119 cm$^{-1}$ and 4011 cm$^{-1}$.

5. The process of claim 1 wherein in step (e) the ratio of the amounts of epoxy and methyl groups is computed and the degree of cure is determined in step (f) by the relationship $$\frac{\left(\frac{E}{M}\right)_i - \left(\frac{E}{M}\right)_f}{\left(\frac{E}{M}\right)_i} \times 100$$

where

E/M is the ratio of epoxy to methyl groups $(E/M)_i$ is the ratio of epoxy to methyl groups in the uncured resin $(E/M)_f$ is the ratio of epoxy to methyl groups in the partially cured resin.

6. The process of claim 1 wherein said infrared beam has a diameter of about 1.25 cm.

7. The process of claim 1 wherein said prepreg sheet moves at a rate of 0.05 to 0.4 m/sec.

8. The process of claim 1 wherein said prepreg sheet is traversed at a rate of about 0.05 m/sec and 90° from the direction of movement of said sheet.

9. The process of claim 1 wherein the predetermined values of (j) are continually measured from a standard prepreg mounted at the edge of said moving sheet of prepreg.

* * * * *

UNITED STATES PATENT AND TRADEMARK OFFICE
CERTIFICATE OF CORRECTION

PATENT NO. : 5,457,319

DATED : October 10, 1995

INVENTOR(S) : Amy L. Moe et al.

It is certified that error appears in the above-identified patent and that said Letters Patent is hereby corrected as shown below:

Column 1, line 27: "fiberglass" should read -- glass fiber --
line 37: "fiberglass" should read -- glass fiber --
Column 3, line 28: "4-3% cure and 4-3% resin" should read
-- ±3% cure and ±3% resin --
line 38: "convened" should read -- converted --
Column 8, line 31: "thorough" should read -- through --
line 47: "said glass fiber" should read    -- glass fibers --

Signed and Sealed this

Fourth Day of June, 1996

Attest:

BRUCE LEHMAN

*Attesting Officer*    *Commissioner of Patents and Trademarks*